United States Patent [19]

Wittkampf

[11] Patent Number: 4,593,695
[45] Date of Patent: Jun. 10, 1986

[54] PACEMAKER WITH IMPROVED TACHYCARDIA TREATMENT MEANS AND METHOD

[75] Inventor: Frederik H. M. Wittkampf, Brummen, Netherlands

[73] Assignee: Vitafin N.V., Dieren, Netherlands

[21] Appl. No.: 603,119

[22] Filed: Apr. 23, 1984

Related U.S. Application Data

[63] Continuation-in-part of Ser. No. 583,175, Feb. 24, 1984, abandoned.

[51] Int. Cl.$^4$ ............................................. A61N 1/36
[52] U.S. Cl. ............................................. 128/419 PG
[58] Field of Search .................... 128/419 PG, 419 PT

[56] References Cited

U.S. PATENT DOCUMENTS

| | | | |
|---|---|---|---|
| 3,939,844 | 2/1976 | Pequignot | 128/419 PG |
| 4,088,139 | 5/1978 | Auerbach | 128/419 |
| 4,088,140 | 5/1978 | Rockland et al. | 128/419 PG |
| 4,163,451 | 8/1979 | Lesnick et al. | 128/419 PG |
| 4,181,133 | 1/1980 | Kolenik et al. | 128/419 PG |
| 4,228,803 | 10/1980 | Rickards | 128/419 PG |
| 4,280,502 | 7/1981 | Baker, Jr. et al. | 128/419 PG |

OTHER PUBLICATIONS

"The Use of QT Interval to Determine Pacing Rate: Early Clinical Experience", by A. F. Richards, et al., Pace, vol. 6, Mar.-Apr. 1983, Part III.

Session III: Current Status of Electrical Control of Tachyarrhythmias; Pace, vol. 7, May-Jun. 1984, Part II, pp. 569-571.

"Panel I: Present State of Industrial Development of Devices", Pace, vol. 7, May-Jun. 1984, Part II, pp. 557-568.

"Clinical Experience With Implantable Devices for Control of Tachyarrhythmias", Pace, vol. 7, May-Jun. 1984, Part II, pp. 548-556.

*Primary Examiner*—William E. Kamm
*Attorney, Agent, or Firm*—Woodcock Washburn Kurtz Mackiewicz & Norris

[57] ABSTRACT

Apparatus and method for treatment of tachycardia, wherein when tachycardia is determined a portion of a patient T-wave is sensed and utilized as indicating the end of the cardiac refractory interval. One or more anti-tachycardia stimuli are delivered in timed relation to the sensed T-wave. The initial T-wave from which the first A-T stimulus is timed may be evoked by delivery of an early stimulus.

22 Claims, 3 Drawing Figures

4,593,695

PACEMAKER WITH IMPROVED TACHYCARDIA TREATMENT MEANS AND METHOD

CROSS-REFERENCE TO RELATED APPLICATION

This application is a continuation-in-part of my pending application Ser. No. 583,175, filed Feb. 24, 1984, titled Pacemaker With Improved Tachycardia Treatment Means And Method and now abandoned.

BACKGROUND OF THE INVENTION

Field of the Invention

The present invention relates to pacemaker systems which incorporate means for sensing and treating tachycardia and, more particularly, a pacemaker having means for sensing an evoked T-wave and thereby determining the end of the cardiac refractory interval, and delivering treatment pulses in timed relation thereto.

BACKGROUND OF THE INVENTION

It is known to incorporate into pacemakers, either external or implantable, means for sensing tachycardia, which is generally defined as an unacceptably high natural heart rate. Such pacemakers also have means for treating the tachycardia, and it is a known technique to apply a burst or bursts of relatively high rate stimulus pulses upon detection of tachycardia.

There is a substantial amount of literature dealing with pacing techniques for terminating ventricular tachycardia. See, for example, the article of Fisher et al, PACE, Vol. 6, September/October 1983, Part II. It is accepted that the critical termination zone, or time during which a delivered stimulus can have effect in terminating the tachycardia, starts after the end of the cardiac refractory period. However, pacemakers have not utilized means to measure the actual cardiac refractory period for this purpose.

My invention is based upon the assumption that the endocardially measured T-wave indicates substantially the end of the cardiac refractory period. This is based upon the fact that the cardiac repolarization causes the T-wave, and only during or after such repolarization can the cells be stimulated again. Although the end of the cardiac refractory period is not absolutely defined, because of the transition period where stimulation threshold declines sharply toward normal values, the sensed endocardial T-wave is the best indicator of the cardiac cell repolarization at the stimulation electrode. Clearly it is a better indicator than the surface T-wave because it originates from only the small area surrounding the electrode. By contrast, the surface T-wave is a result of the total effect of all of the heart cell repolarizations. Thus, the prior existing problem which this invention solves is the accurate timing of anti-tachycardia stimulation pulses to occur in timed relation to cardiac repolarization, so as to optimize the effect of such pulses in breaking up the tachycardia.

SUMMARY OF THE INVENTION

It is an object of this invention to provide an improved method and means of treating tachycardia.

It is another object of this invention to provide an implantable pacemaker with means for determining the existence of tachycardia and for treating the tachycardia.

It is another object of this invention to provide an improved tachycardia termination method based upon endocardial T-wave sensing as a basis for timing anti-tachycardia stimulus pulses.

It is another object of this invention to provide a programmed series of anti-tachycardia stimulus pulses, each such pulse being in a given timed relation to the just preceding heart repolarization.

In accordance with the above objects, my invention provides a method and means of treating a sensed tachycardia, comprising delivering an early stimulus before an expected natural beat so as to evoke a heartbeat response including a T-wave, determining the timing of the evoked T-wave and then delivering one or more treatment stimuli in timed relation to the T-wave. The treatment may involve a single anti-tachycardia stimulus or a series thereof, each stimulus in the series being timed in relation to the just preceding cardaic repolarization as measured by the sensed endocardial T-wave.

DETAILED DESCRIPTION OF THE PREFERRED EMBODIMENTS

Figure 1:
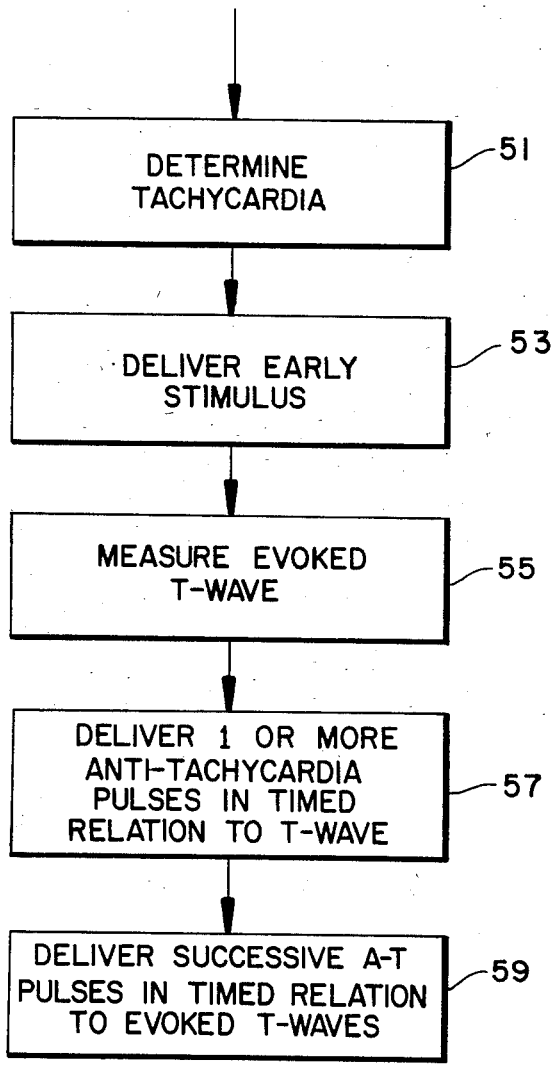
FIG. 1 is a flow diagram showing the basic steps of the method of this invention.

Referring now to FIG. 1, there is shown a brief diagram which outlines the major steps of the method of this invention. At block 51, the existence of tachycardia is determined. This may be done in any one of a number of conventional ways that are presently employed in commercially available devices. A standard technique is to define an upper rate limit and count successive natural heartbeats or a proportion of heartbeats that are above the upper rate limit. In accordance with this invention, when tachycardia has been determined, the device delivers an early stimulus so as to produce an evoked response. For example, in a pacemaker such as the DPG pacemaker of the assignee of this invention, the interval T between pulses is tracked and stored, from which of course the rate can be determined. If the tachycardia is thus determined to be existing with natural heartbeats at an interval of approximately T, a stimulus can be interjected by timing out a pacing interval which is $T - \Delta T$, where $\Delta T$ is a safe enough interval to ensure delivery of the stimulus before the next natural heartbeat. Following this, the T-wave portion of the evoked response is measured, i.e. sensed. In the practice of this invention, the measurement of the T-wave may be done by determining the peak of the T-wave, or a point on the down slope where the T-wave has dropped from its peak to a predetermined fraction thereof. Although measurement of the peak is a preferred technique, other considerations may be used in terms of processing the T-wave to make an evaluation of the effective end of the refractory period.

After having detected the evoked T-wave, it is then possible to optimally deliver an anti-tachycardia (A-T) stimulus pulse in timed relation to the T-wave, as indicated at block 57. Thus, a single pulse or two or more pulses timed relative to the measured T-wave can be delivered for the purpose of terminating the tachycardia. Assuming that the refractory period ends after the measured portion of the T-wave, the first treatment stimulus can be delivered very shortly thereafter, with succeeding stimuli delivered in accordance with a desired algorithm. Further, as indicated at block 59, the termination treatment can be continued by delivering a series of stimuli each timed in relation to a preceding evoked T-wave. Generally, it is desirable that each following stimulus of a series of A-T stimulus pulses be delivered after a shorter interval, i.e., the time from the second pulse to the third is shorter than from the first pulse to the second, etc.

While the preferred form of the invention incorporates the delivery of an early stimulus so as to evoke a measureable T-wave, it is to be understood that the method and apparatus of the invention also covers delivering A-T pulses in timed relation to a sensed natural T-wave. However, since the T-wave following a delivered stimulus is larger than a natural T-wave, and therefore more easily detected and measured, in the preferred embodiment the first early stimulus is to evoke a T-wave, and the following stimuli are A-T stimuli designed to capture the heart at a time which breaks up the tachycardia.

As used in this specification, reference to determining the occurrence of a T-wave, either evoked or natural, refers to measuring a predetermined portion of the T-wave, e.g. the peak or any other predetermined portion of the T-wave. While the natural cardiac refractory period is a parameter which varies with the preceding cycle, the invention takes advantage of the fact that an effective A-T stimulus pulse can be timed relative to detection of a given portion of the T-wave.

Figure 2A:
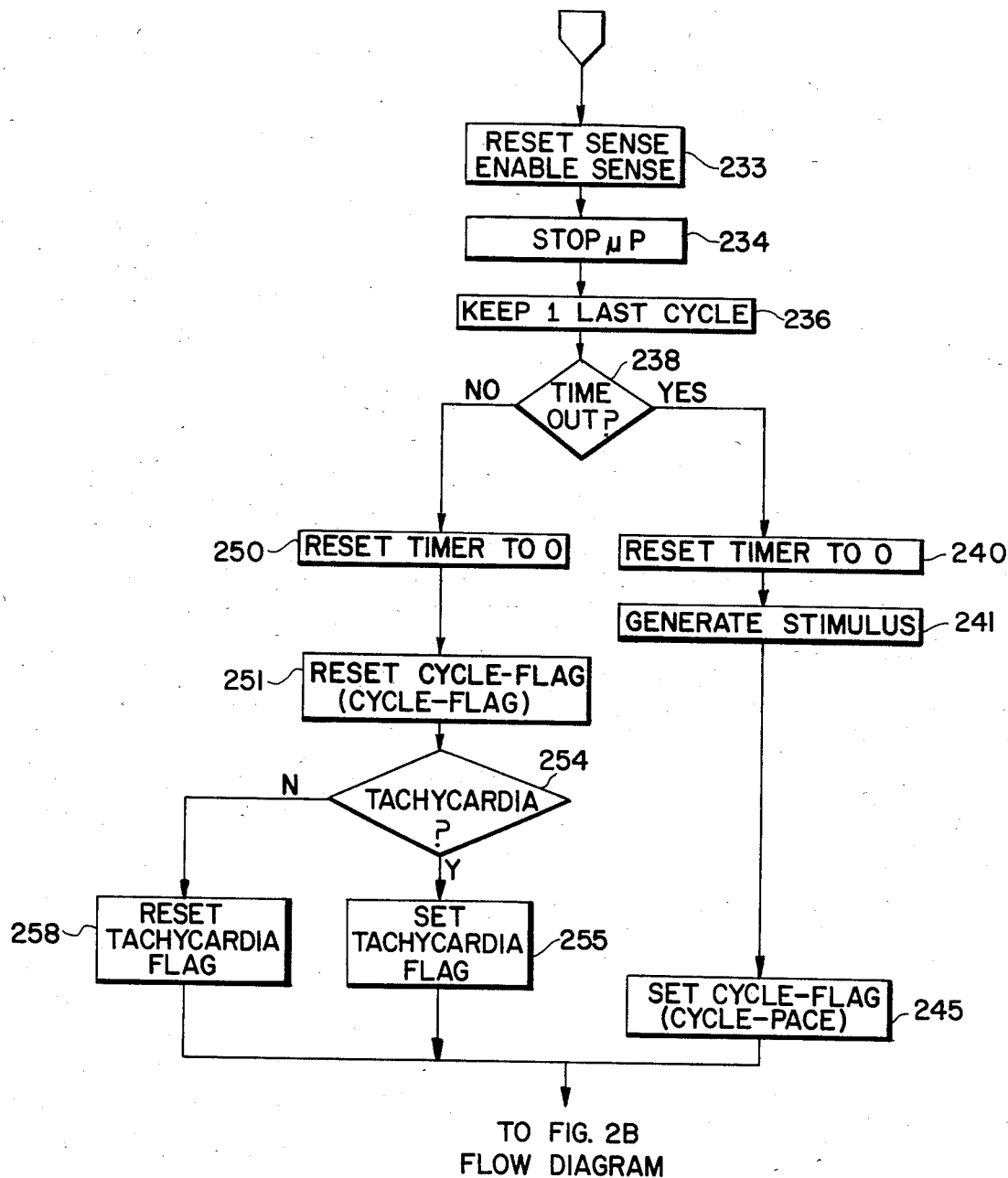
FIGS. 2A and 2B combined present a more detailed flow diagram carried out by a microprocessor controlled pacemaker in accordance with the apparatus and method of this invention.
Figure 2B:
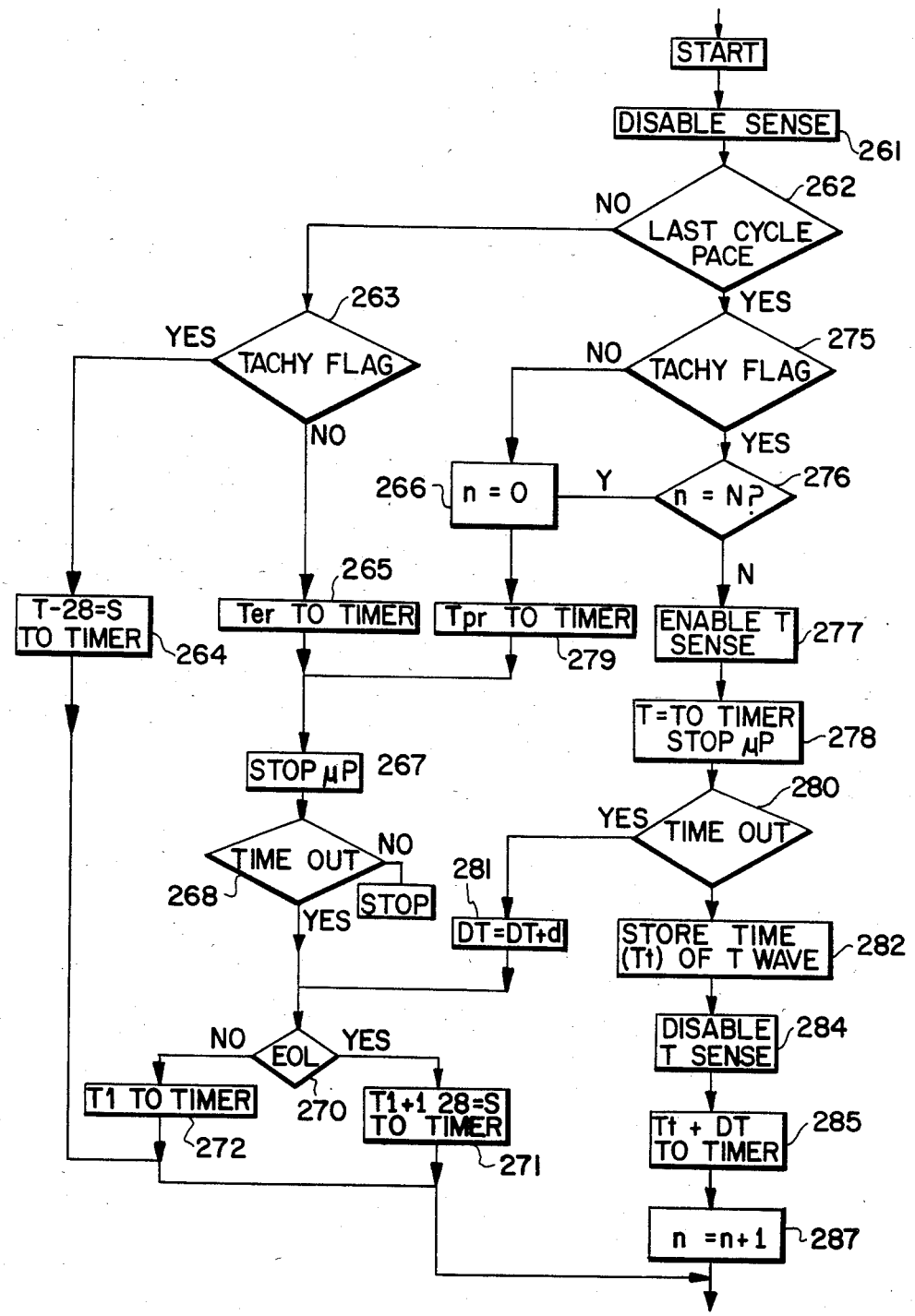

Referring now to FIGS. 2A and 2B, there is shown a more detailed block diagram of steps taken in a microprocessor controlled pacemaker such as the DPG pacemaker of the assignee of this invention. Reference is made to U.S. Pat. Nos. 4,503,857 and 4,539,991, assigned to the same assignee, which disclose embodiments of a microprocessor implantable pacemaker and which are incorporated by reference. Reference is also made to U.S. Pat. Nos. 4,228,803 and 4,305,396 which describe operation of embodiments of a $T_x$ pacemaker, wherein the T-wave time is measured relative to the preceding stimulus, which patents are also incorporated herein by reference.

Referring first to FIG. 2A, the program starts at the point where the pacer is going to wait for either time out of the pacing interval so as to deliver a stimulus pulse, or for detection of a sensed natural heartbeat signal, e.g. QRS. At block 233 the sense circuitry is enabled and at 234 the microprocessor stops. When it starts again, due to either a sensed QRS or time out of the timer, the microprocessor keeps the time T of the last cycle, as indicated at 236. At block 238, the pacemaker determines whether or not there has been a time out, and stores this information. If there has been a time out, meaning that no natural heartbeat has been detected and a stimulus is to be delivered, the program branches to the right as shown. The timer is reset to zero at 240, and the stimulus is generated and delivered at block 241. The cycle flag is then set to cycle=pace at block 245, following which the routine goes to block 260, at the top of FIG. 2B.

Returning to block 238, if there has been no time out, indicating that a natural heartbeat has been detected, the program branches to the left. The timer is reset to zero at 250, and the cycle flag is set to cycle=sense at 251. At block 254 it is determined whether or not the patient exhibits tachycardia. This is done in a conventional manner as discussed above, and it is to be understood that block 254 may encompass further logical steps such as determining the number of successive natural heartbeats observed at a rate exceeding the predetermined tachycardia rate. If the answer is yes, the tachycardia flag is set at block 255. If the answer is no, the tachycardia flag is reset at block 258. The algorithm of block 254 also determines when a tachycardia has terminated, in which case also the flag is reset at block 258.

Referring now to the top of FIG. 2B, at block 261 the QRS sense circuitry is disabled. At block 262 it is determined whether the last cycle ended with a sense or a pace. If sense, the program branches to the left and at block 263 checks to see whether the tachycardia flag is set. If yes, at block 264 a time T−20 ms is put into the timer. Thus, the timer is set to time out 20 ms before the next expected natural heartbeat, assuming that the tachycardia rate is substantially constant. Of course, the time that is subtracted from the interval T can be made larger or smaller, as desired. Following setting of the timer, the program branches and returns to the top of FIG. 2A, It is thus seen that in this condition, and assuming the early stimulus is delivered, during the next cycle the microprocessor takes a different path at block 262.

Returning to block 263, if the tachycardia flag is not set, the escape refractory interval time $T_{er}$ is put into the timer at 265, the microprocessor stops at 267 and waits for a time out at 268. Thereafter, at block 270 it is determined whether the pacemaker is in an end-of-life (EOL) condition. If no, the normal pacing interval $T_i$ is put into the timer at 272. If yes, the pacing interval is incremented by 100 ms before being put into the timer, as illustrated at 271.

Referring back to block 262, if it is determined that the last cycle was a pace cycle, at block 275 it is determined whether the tachycardia flag is set. If not, the program branches to block 279, where the pacing refractory interval $T_{pr}$ is put into the timer, following which the routine goes to block 268. If the tachycardia flag is set, the routine proceeds to block 276 where it is determined if n=N. If yes, meaning that a predetermined number N of A-T stimuli have been delivered, the program then branches to block 279. If no, meaning that one or more A-T stimuli are to be delivered, the program continues to block 277 where the T-wave sense circuitry is enabled. A T-wave sensing window is defined, ending at time $T_W$, and $T_W$ is put into the timer as indicated at block 278. The microprocessor then stops and waits. At block 280, it is determined whether there has been a time out, i.e., if a T-wave has been sensed. If no, indicating that a T-wave has been sensed, the time Tt of the T-wave is stored at block 282. Following this, the T sense circuitry is disabled at 284, and the time $T_T+D_T$ is set into the timer at 285. The value of DT is chosen as the desired time from the end of the cardiac refractory period to the time of delivery of the A-T stimulus pulse, It is to be understood that DT is a matter of design choice, and may vary as a function of n, the number of the A-T pulse in the programmed series of A-T pulses. Next, at block 287, the number n is incremented by 1, The program then recycles to the top of FIG. 2A, where an A-T stimulus is delivered at block 241 following time out of the time $T_t+DT$ at block 238. The procedure is repeated N times until the program branches from block 276 to 266, where the value of n is reset to zero.

Returning to block 280, if there has been a time out, the program branches to block 281 where the value of DT is incremented by a predetermined value d. In the event that no T-wave is sensed following a preceding stimulus, this could mean that DT is too small, and accordingly the delay following detection of the T-wave is incremented.

The flow diagram of FIGS. 2A and 2B discloses a preferred technique of a first early stimulus which is not intended to be an anti-tachycardia pulse, but serves only to evoke a heartbeat so that a T-wave can be sensed, for purposes of establishing timing of the succeeding A-T pulses. After the first A-T pulse, successive A-T stimulus pulses are each timed in relation to the T-wave of the heartbeat evoked by the prior A-T stimulus. Alternately, this invention covers sensing the Q-T interval one or more beats in advance, and the timing the generation and delivery of A-T pulses from a sensed QRS, taking into account the prior measured Q-T interval. Alternately, one or more A-T pulses can be timed solely from a first QRS or T-wave, using the prior measured Q-T interval in the algorithm, i.e., without sensing the T-wave of each succeeding evoked heartbeat. Further, at block 280, in the event that no T-wave is sensed, the program can use the prior measured Q-T interval as the current value of Tt. Thus, it is seen that the invention embraces a number of different alternate methods for controlling the geneation of A-T pulses and determine the time relation to the just prior cardaic repolarization.

I claim:

1. A method of terminating tachycardia in a patient, comprising
determining the occurence of tachycardia;
determining the timing of a T-wave portion of a patient heartbeat; and
delivering an A-T treatment stimulus a predetermined time after said T-wave portion.

2. The method as described in claim 1, wherein the step of determining the timing of said T-wave portion includes delivering an early stimulus before a next expected natural heartbeat, thereby evoking said heartbeat having said T-wave portion.

3. The method as described in claim 2, comprising determining the timing of the T-wave portion of each evoked heartbeat following a delivered A-T stimulus, and delivering a respective other A-T stimulus in timed relation to each said determined T-wave portion so long as tachycardia continues.

4. The method as described in claim 2, comprising delivering a plurality of A-T treatment stimuli, each in timed relation to the determined timing of said evoked T-wave.

5. The method as described in claim 4, comprising delivering said plurality of stimuli in succession with each succeeding stimulus following the preceding stimulus by a time interval which is smaller than the previous such interval.

6. The method as described in claim 1, comprising determining the timing of a T-wave portion of a heartbeat evoked by said A-T stimulus, and delivering another A-T stimulus in timed relation to said T-wave portion.

7. The method as described in claim 1, comprising sensing the T-wave portion of the heartbeat evoked by said A-T treatment stimulus and delivering a second A-T treatment stimulus in timed relation to said sensed T-wave portion, and as long as said tachycardia continues, sensing the occurence of each succeeding T-wave and delivering an A-T treatment stimulus in timed relation thereto.

8. The method as described in claim 7, wherein each step of delivering an A-T treatment stimulus comprises delivering only one such stimulus in timed relation to a just prior determined T-wave.

9. Apparatus for treating tachycardia in a patient, comprising
means for determining the occurrence of tachycardia;
means for determining the occurrence of a T-wave of a patient heartbeat; and
means for delivering at least one A-T treatment stimulus in timed relation to said determined T-wave.

10. The apparatus as described in claim 9, wherein said apparatus also comprises means for delivering pacing pulses to said patient on a demand basis in the absence of tachycardia.

11. The apparatus as described in claim 9, further comprising means enabled following determination of patient tachycardia for delivering an early stimulus before an expected natural heartbeat, and means for determining the timing of the evoked T-wave following said delivered stimulus.

12. Apparatus for treating tachycardia in a patient, comprising means for determining the occurence of tachycardia and A-T stimulus means for delivering anti-tachycardia stimulus pulses, characterized by
patient timing means for timing the occurence of at least a portion of a T-wave, and
control means for controlling said A-T stimulus means to deliver at least one anti-tachycardia stimulus pluse a predetermined time following said timed T-wave portion.

13. The apparatus as described in claim 12, further characterized by means for sensing the timing of a succeeding T-wave evoked by an anti-tachycardia stimulus and wherein said control means controls said A-T stimulus means to deliver an anti-tachycardia stimulus pulse in a predetermined timed relation to said succeeding T-wave.

14. The apparatus as described in claim 12, further characterized by said control means controlling the delivery of a series of n anti-tachycardia stimulus pulses.

15. The apparatus as described in claim 14, wherein each stimulus of said series is delivered in timed relation to a respective preceding evoked T-wave.

16. The apparatus as described in claim 12, further characterized by evoking means for evoking a heartbeat when tachycardia is determined, and wherein said timing means times at least a portion of the T-wave portion of said evoked heartbeat.

17. The apparatus as described in claim 16, further characterized by means for sensing the timing of a succeeding T-wave evoked by an anti-tachycardia stimulus and wherein said control means controls said A-T stimulus means to deliver an anti-tachycardia stimulus pulse in a predetermined timed relation to said succeeding T-wave.

18. The apparatus as described in claim 17, further characterized by said control means controlling the delivery of a series of n anti-tachycardia stimulus pulses.

19. Apparatus for treating tachycardia in a patient, comprising means for determining the occurence of tachycardia and A-T means for delivering one or more anti-tachycardia pulses for the purpose of terminating said tachycardia, characterized by control means for controlling said A-T means to deliver at least one said anti-tachycardia pulse at a time following a just prior cardiac repolarization by a predetermined delay.

20. The apparatus as described in claim 19, further characterized by means for determining the Q-T time of a patient heartbeat during tachycardia and utilizing said Q-T time to determine the timing of said first anti-tachycardia pulse.

21. The apparatus as described in claim 19, wherein said control means is further characterized by timing means for timing out a predetermined delay following said just prior cardiac repolarization.

22. The apparatus as described in claim 21, comprising means for adjusting said predetermined delay.

* * * * *